US00PP28536P3

(12) United States Plant Patent
Martin

(10) Patent No.: US PP28,536 P3
(45) Date of Patent: Oct. 17, 2017

(54) ***BEGONIA* PLANT NAMED 'AUEMB'**

(50) Latin Name: ***Begonia* hybrid**
Varietal Denomination: AUEMB

(71) Applicant: Byron E. Martin, Danielson, CT (US)

(72) Inventor: Byron E. Martin, Danielson, CT (US)

( * ) Notice: Subject to any disclaimer, the term of this patent is extended or adjusted under 35 U.S.C. 154(b) by 0 days.

(21) Appl. No.: 14/998,974

(22) Filed: Mar. 11, 2016

(65) Prior Publication Data

US 2017/0265364 P1 Sep. 14, 2017

(51) Int. Cl.
*A01H 5/02* (2006.01)

(52) U.S. Cl.
USPC ..... Plt./343

(58) Field of Classification Search
USPC ..... Plt./343
See application file for complete search history.

*Primary Examiner* — Keith Robinson

(57) ABSTRACT

A new cultivar of *Begonia* plant named 'AUEMB' that is characterized by pink flowers and large leaves that are orange on the upper-side and red-orange on the under-side.

2 Drawing Sheets

Botanical classification: *Begonia* hybrid.
Variety denomination: 'AUEMB'.

BACKGROUND OF THE INVENTION

The present invention relates to a new and distinct cultivar of *Begonia* plant botanically known as *Begonia* hybrid and hereinafter referred to by the cultivar name 'AUEMB'.

'AUEMB' originated from the crossing of the female or seed parent *Begonia* 'Angel Glow' (not patented) and the male or pollen parent *Begonia* 'Marmaduke' (not patented). The crossing was conducted in 2012 in Danielson, Conn. The resulting seeds were subsequently planted and grown. The cultivar 'AUEMB' was selected by the inventor in 2013 in a controlled environment as a single plant within the progeny of the stated cross in a cultivated area of Danielson, Conn.

Asexual reproduction of the new cultivar 'AUEMB' first occurred by tissue culture in 2013 in Danielson, Conn. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Begonia* cultivar 'AUEMB'. These traits in combination distinguish 'AUEMB' as a new and distinct cultivar apart from other existing known varieties of *Begonia*.

1. *Begonia* 'AUEMB' exhibits large leaves.
2. *Begonia* 'AUEMB' exhibits leaves that are orange on the upper-side and red-orange on the under-side.
2. *Begonia* 'AUEMB' exhibits pink flowers.

The closest comparison cultivar is *Begonia* 'Northern Lights' (not patented). 'AUEMB' is distinguishable from 'Northern Lights' by the following characteristics:

1. *Begonia* 'AUEMB' exhibits smaller leaves than the leaves of 'Northern Lights'.

2. *Begonia* 'AUEMB' exhibits leaves that are orange on the upper-side and red-orange on the under-side. In contrast, the leaves of 'Northern Lights' are yellow-green and speckled with red blotches on both sides.
3. *Begonia* 'AUEMB' exhibits veins on the under-side of the leaf that are smooth. The leaf veins on the under-side of the leaves of 'Northern Lights' have red hairs.
4. *Begonia* 'AUEMB' exhibits pink flowers. The flowers of 'Northern Lights' are white.

'AUEMB' is distinguishable from the female or seed parent *Begonia* 'Angel Glow' by the following characteristics:

1. *Begonia* 'AUEMB' exhibits larger leaves than the leaves of 'Angel Glow'.
2. *Begonia* 'AUEMB' exhibits leaves that are orange on the upper-side and red-orange on the under-side. In contrast, the leaves of 'Angel Glow' are red-orange with green veins on both sides.
3. *Begonia* 'AUEMB' exhibits a larger overall plant height than the overall plant height of 'Angel Glow'.

'AUEMB' is distinguishable from the male or pollen parent *Begonia* 'Marmaduke' by the following characteristics:

1. *Begonia* 'AUEMB' exhibits smaller leaves than the leaves of 'Marmaduke'.
2. *Begonia* 'AUEMB' exhibits leaves that are orange on the upper-side and red-orange on the under-side. The upper-side leaves are smooth with no hairs. In contrast, the leaves of 'Marmaduke' are red-orange, undulating and the upper-side is covered with fine hairs.
3. *Begonia* 'AUEMB' exhibits a smaller overall plant height than the overall plant height of 'Marmaduke'.

BRIEF DESCRIPTION OF THE DRAWING

The accompanying photographs illustrate the distinguishing traits of *Begonia* 'AUEMB'.

Figure 1:
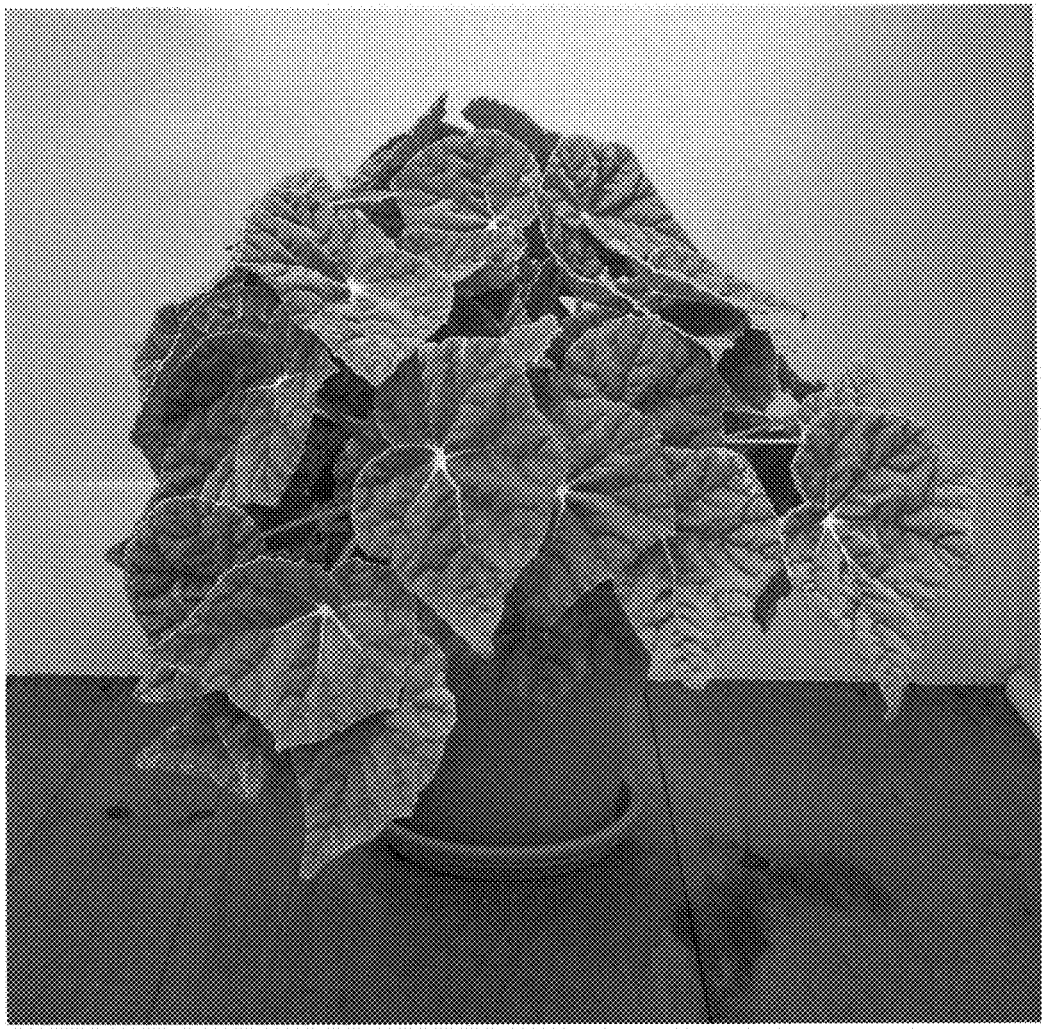
FIG. 1 shows an overall view of a 2 year old plant.
Figure 2:
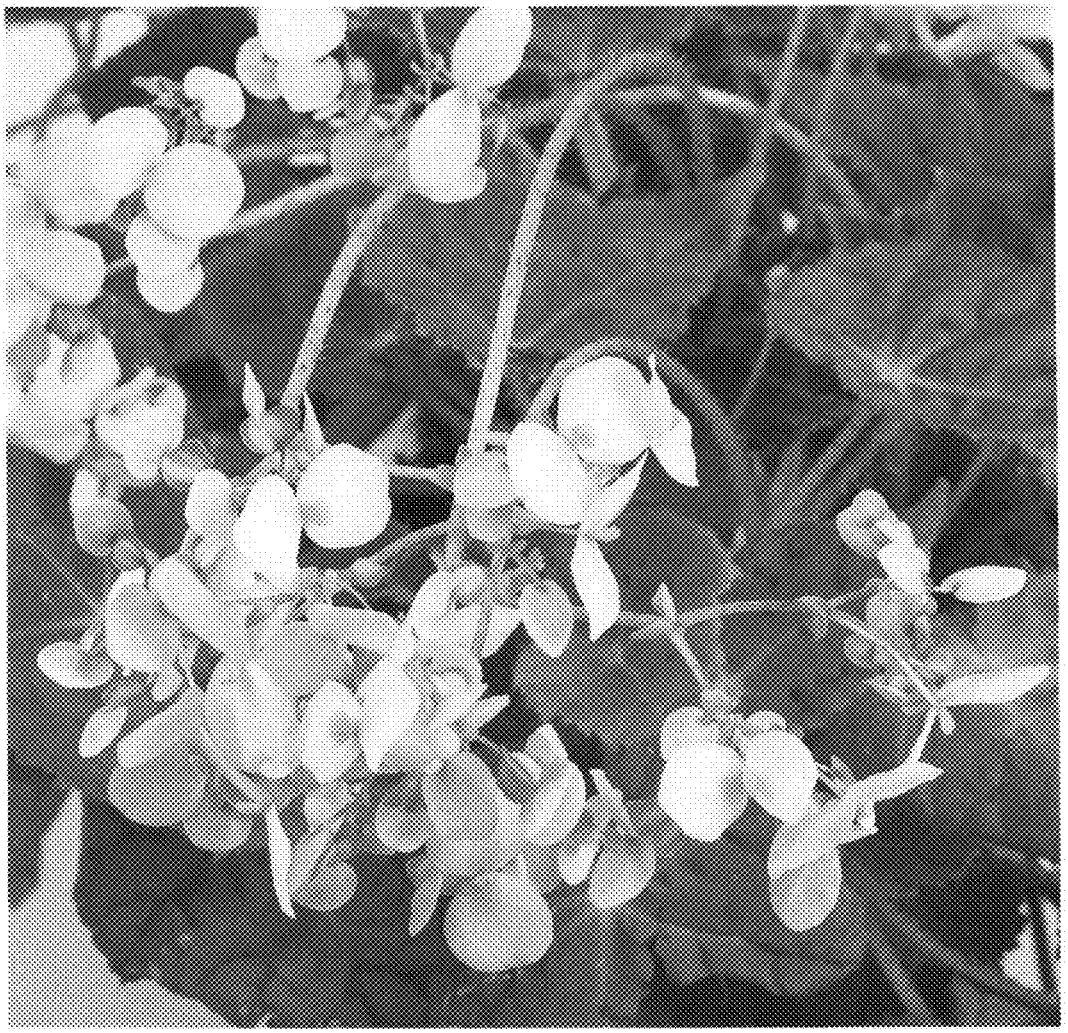
FIG. 2 shows an enlarged view of the flowers.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Begonia* cultivar named 'AUEMB'. Data was collected in Danielson, Conn. from 2 year old greenhouse grown plants outdoors in 6 inch diameter containers. The time of year was Summer and the average temperature was 23 degrees Centigrade during the day and 18 degrees Centigrade at night. No photoperiodic treatments or growth retards were used. Color determinations are in accordance with The Royal Horticultural Society Colour Chart 2007 edition, except where general color terms of ordinary dictionary significance are used. The growing requirements are similar to the species. 'AUEMB' has not been tested under all possible conditions and phenotypic differences may be observed with variations in environmental, climatic, and cultural conditions, however, without any variance in genotype.

Botanical classification: *Begonia* hybrid 'AUEMB'.
Annual or perennial: Perennial.
Parentage: 'AUEMB' is the product of the female or seed parent *Begonia* 'Angel Glow' and the male or pollen parent *Begonia* 'Marmaduke'.
Plant shape: Mounding.
Growth habit: Spreading rhizome.
Suitable container size: 6 inch diameter pots.
Plant height: 20 cm. in height.
Plant width: 27 cm. in width.
Vigor: Moderate.
Low temperature tolerance: 5° Centigrade.
High temperature tolerance: 35° Centigrade.
Propagation: Leaf wedges and tissue culture.
Time to initiate roots (summer): 14 days at 28° C.
Time to initiate roots (winter): 20 days at 20° C.
Time to produce a rooted cutting: 28 days at 28° C.
Time to produce a rooted cutting: 45 days at 20° C.
Crop time: Approximately 3 to 4 months.
Root system: Fine and fibrous.
Rhizomes:
- *Dimensions.*—2.0 cm. in length and 0.3 cm. in diameter.
- *Texture.*—Covered with rough scales.
- *Color.*—N199B.

Foliage:
- *Leaf arrangement.*—Single leaves arise directly from rhizome.
- *Quantity of leaves per plant.*—Approximately 58.
- *Leaf shape.*—Unequal reniform.
- *Leaf apex.*—Acute.
- *Leaf base.*—Hastate, slightly overlapping.
- *Leaf length.*—12.0 cm. in length.
- *Leaf width.*—9.0 cm. in width.
- *Texture (both surfaces).*—Smooth.
- *Pubescence.*—Absent.
- *Leaf margin.*—Serrulate.
- *Venation pattern.*—Palmate.
- *Young leaf color (upper surface).*—N172C.
- *Young leaf color (lower surface).*—N34B.
- *Mature leaf color (upper surface).*—N172B.
- *Mature leaf color (lower surface).*—N34B.
- *Vein color (upper surface).*—151D.
- *Vein color (under surface).*—20A.
- *Leaf attachment.*—Petiolate.
- *Petiole dimensions.*—14.0 cm. in length, and 4.0 mm. in diameter.
- *Petiole color.*—145B with flecks of 43B.

Flower:
- *Inflorescence type.*—Dichotomous cymes.
- *Inflorescence dimensions.*—30.0 cm. in length and 18.0 cm. in width.
- *Quantity of flowers per inflorescence.*—Average 32.
- *Quantity of flower buds per lateral stem.*—25.
- *Quantity of flowers and buds per plant.*—Approximately 250.
- *Natural flowering season.*—Spring.
- *Fragrance.*—Absent.
- *Flower bud length.*—12 mm.
- *Flower bud diameter.*—12 mm.
- *Flower bud shape.*—Ovate.
- *Bud color.*—54C.
- *Flower aspect.*—Outward, drooping.
- *Flower arrangement.*—2 opposed tepals.
- *Flower longevity.*—Approximately 4 weeks.
- *Male flowers.*—Dimensions: 30 mm. in diameter and 11 mm. in height. Number of tepals: 2. Fused or unfused: Unfused. Tepal shape: Ovate. Tepal margin: Entire. Tepal apex: Obtuse. Tepal base: Rounded. Tepal texture: Glabrous both surfaces. Tepal dimensions: 18 mm. in length and 12 mm. in width. Tepal color when opening (upper side): 55C, margins 54B. Tepal color when opening (under side): 55C, margins 54B. Tepal color fully opened (upper side): 55C. Tepal color fully opened (under side): 55C. Tepal Self-cleaning or persistent: Self-cleaning.
- *Female flowers.*—Dimensions: 17 mm. in diameter and 8 mm. in height. Number of tepals: 2. Fused or unfused: Unfused. Tepal shape: Ovate. Tepal margin: Entire. Tepal apex: Obtuse. Tepal base: Rounded. Tepal texture: Glabrous both surfaces. Tepal dimensions: 9 mm. in length and 5 mm. in width. Tepal color when opening (upper side): 55C, margins 54B. Tepal color when opening (under side): 55C, margins 54B. Tepal color fully opened (upper side): 55C. Tepal color fully opened (under side): 55C. Tepal Self-cleaning or persistent: Self-cleaning.

Peduncle:
- *Peduncle dimensions.*—24 cm. in length and 4 mm. in diameter.
- *Peduncle strength.*—Moderate.
- *Peduncle color.*—145C with flecks of 43B.
- *Peduncle texture.*—Covered with stiff hairs, 3 mm. in length, color N155A.

Reproduction organs:
- *Stamen number.*—13.
- *Anther shape.*—Elliptic.
- *Anther length.*—2.0 mm.
- *Anther color.*—6A.
- *Amount of pollen.*—Moderate.
- *Pistil number.*—3.
- *Pistil length.*—4.0 mm.
- *Stigma shape.*—U shaped.
- *Stigma color.*—7B.
- *Style length.*—2.0 mm.
- *Style color.*—52B.
- *Ovary color.*—52B.

Fruit and seed: Fruit and seed production have not been observed to date.
Disease and pest resistance: Disease and pest resistance have not been observed to date.

The invention claimed is:

1. A new and distinct variety of *Begonia* plant named 'AUEMB' as described and illustrated.

* * * * *